US009599568B2

(12) United States Patent
Fabre et al.

(10) Patent No.: US 9,599,568 B2
(45) Date of Patent: Mar. 21, 2017

(54) METHOD OF DETERMINING THE APPEARANCE OF LOSSES OF COHESION IN A TRANSPARENT CERAMIC COATING LAYER FORMED ON A SUBSTRATE

(75) Inventors: Gregory Fabre, Bournezeau (FR); Jean-Yves Guedou, Le Mee sur Seine (FR); Vincent Guipont, Villeblevin (FR); Michel Christian Marcel Jeandin, Paris (FR)

(73) Assignee: SNECMA, Paris (FR)

( * ) Notice: Subject to any disclaimer, the term of this patent is extended or adjusted under 35 U.S.C. 154(b) by 260 days.

(21) Appl. No.: 14/238,006

(22) PCT Filed: Aug. 7, 2012

(86) PCT No.: PCT/FR2012/051856
§ 371 (c)(1),
(2), (4) Date: Mar. 14, 2014

(87) PCT Pub. No.: WO2013/021134
PCT Pub. Date: Feb. 14, 2013

(65) Prior Publication Data
US 2014/0185916 A1    Jul. 3, 2014

(30) Foreign Application Priority Data
Aug. 10, 2011 (FR) ..................... 11 57283

(51) Int. Cl.
*G01N 21/84* (2006.01)
*G01N 19/04* (2006.01)
*G06T 7/00* (2006.01)

(52) U.S. Cl.
CPC ......... *G01N 21/8422* (2013.01); *G01N 19/04* (2013.01); *G06T 7/0004* (2013.01); *G01N 2021/8427* (2013.01)

(58) Field of Classification Search
CPC ............... G01N 19/04; G01N 21/8422; G01N 2021/8427
See application file for complete search history.

(56) References Cited

U.S. PATENT DOCUMENTS 5,015,502 A    5/1991 Strangman et al.
5,696,583 A *  12/1997 Yoon .................. G01B 11/0633
                                          356/497
5,843,585 A    12/1998 Alperine et al.
(Continued)

FOREIGN PATENT DOCUMENTS

FR    2 926 137    7/2009

OTHER PUBLICATIONS

International Search Report Issued Dec. 5, 2012 in PCT/FR12/051856 Filed Aug. 7, 2012.

*Primary Examiner* — Paul West
(74) *Attorney, Agent, or Firm* — Oblon, McClelland, Maier & Neustadt, L.L.P.

(57) ABSTRACT

A method of determining the appearance of losses of cohesion in a transparent ceramic coating layer (16) formed on a substrate (10), the method comprising the steps that consist firstly in looking for an image representative of a separation zone, if any, between the ceramic layer and the substrate, and secondly in analyzing the detected image, if any, with the image being viewed optically at particular wavelengths that are greater than or equal to 500 nm.

5 Claims, 1 Drawing Sheet

(56) References Cited

U.S. PATENT DOCUMENTS

| | | | | |
|---|---|---|---|---|
| 6,285,449 B1 * | 9/2001 | Ellingson | ............... | G01N 21/95 356/237.1 |
| 2004/0149026 A1 | 8/2004 | Potyrailo et al. | | |
| 2011/0189379 A1 * | 8/2011 | Ortner | ................. | G01N 25/72 427/9 |
| 2012/0034491 A1 * | 2/2012 | Hongoh | ................ | C04B 41/009 428/697 |

* cited by examiner

METHOD OF DETERMINING THE APPEARANCE OF LOSSES OF COHESION IN A TRANSPARENT CERAMIC COATING LAYER FORMED ON A SUBSTRATE

CROSS-REFERENCE TO RELATED APPLICATIONS

This application is a National Stage of PCT/FR2012/051856, which was filed on Aug. 7, 2012. This application is based upon and the claims the benefit of priority to French Application No. 11 57283, which was filed on Aug. 10, 2011.

BACKGROUND OF THE INVENTION

The present invention relates to the general field of non-destructive inspection of a transparent ceramic thermal barrier layer formed on a substrate.

A particular field of application of the invention is that of adhesion testing for coatings such as those used for hot parts in a turbine, such as for nozzle vanes or for rotor blades in a high pressure turbine.

It is known to provide parts made of monocrystalline metal alloy with a thermal barrier in the form of a ceramic layer. A ceramic that is commonly used for this purpose is zirconia $ZrO_2$, possibly stabilized with yttrium. Such a thermal barrier is typically formed by physical vapor deposition (PVD), and in particular by electron beam PVD (EBPVD), which gives a columnar structure to the thermal barrier.

A bonding underlayer is interposed between the substrate of monocrystalline metal alloy and the thermal barrier, which has a function of withstanding oxidation, and which enhances adhesion of the thermal barrier so as to enable it to present good resistance to spalling.

A known bonding underlayer is made up of a nickel and/or cobalt aluminide that has been modified with a platinum type metal, and that may possibly also include, in the vicinity of the interface with the thermal barrier, a metal that promotes the formation of a film of alumina ($Al_2O_3$) on which the thermal barrier is anchored.

For monocrystalline metal alloy parts provided with a thermal barrier formed by a ceramic oxide layer, and more generally for substrates coated with a ceramic layer, it is desirable to have available a method that makes it possible in non-destructive manner to determine whether any losses of cohesion have appeared between the oxide layer and the substrate.

Document FR 2 926 137 discloses a method of determining the adhesion of a ceramic coating layer, which method consists in applying a laser pulse to the substrate coated in the ceramic layer, in searching for an image representative of a zone of separation, if any, between the ceramic layer and the substrate, and in analyzing the detected image, if any. In the absence of separation of the ceramic layer, and since this layer is transparent, it leaves visible the underlayer, which is gray in color. In contrast, in the event of the ceramic layer being separated as a result of the laser pulse, a layer of air is present under the separated portion of the ceramic layer, which gives rise to a spot that is pale. The area of the spot represents the magnitude of the separated portion.

In general, it is essential to be able to measure accurately the spots observed at the interface between the ceramic coating layer and the substrate in order to be able to estimate the sizes of the corresponding separations. Unfortunately, given the poor contrast that exists between the color of the spot (generally whitish) and the gray color of the underlying layer, those spots are often difficult to observe and define with the naked eye or while using any simple optical technique.

OBJECT AND SUMMARY OF THE INVENTION

A main object of the present invention is thus to mitigate such drawbacks by seeking to improve the observation of the spots that appear when separation occurs between the substrate and the ceramic coating.

This object is achieved by a method of determining the appearance of losses of cohesion in a transparent ceramic coating layer formed on a substrate, the method comprising the steps that consist in looking for an image representative of a separation zone, if any, between the ceramic layer and the substrate, and analyzing the detected image, if any, which image is viewed optically at particular wavelengths longer than or equal to 500 nanometers (nm).

The Applicant has found that observing the image at wavelengths longer than or equal to 500 nm makes it possible to eliminate short wavelength noise that prevents it being possible to distinguish zones with separation from zones without separation. Thus, even before carrying out image processing, if any, the images that are obtained present strong contrast between pale zones corresponding to spots and gray zones corresponding to no separation. As a result, the method of the invention makes it possible to detect spots reliably and also makes it possible, subsequently, to determine their dimensions accurately in order to deduce their size.

It should be observed that viewing the image at particular wavelengths is not a kind of image processing that can be applied after the image has been acquired, but is indeed a particular image acquisition process that eliminates the wavelengths belonging to noise.

When the transparent ceramic consists in zirconia obtained by a plasma deposition process, the particular wavelengths are preferably longer than or equal to 600 nm. The Applicant has found that for zirconia of this type, wavelengths longer than or equal to 600 nm show up more clearly the differences between zones with spots and zones without spots.

When transparent ceramic consists in zirconia obtained by an EBPVD deposition process, the particular wavelengths are preferably longer than or equal to 500 nm. It has also been found that for this type of columnar structure zirconia, wavelengths longer than or equal to 500 nm are the best at showing up the spots visually.

Various implementations are possible. Thus, the coating layer may be subjected to narrow spectrum lighting at the particular wavelengths, the image being captured by a camera. Alternatively, the coating layer may be subjected to white lighting, the image being captured by a camera with a filter at the particular wavelengths being interposed between said camera and the substrate. Also alternatively, the coating layer may be subjected to white lighting, the image being captured by a camera having optical sensors adjusted to the particular wavelengths.

BRIEF DESCRIPTION OF THE DRAWING

Other characteristics and advantages of the present invention appear from the following description made with reference to the accompanying drawing, which shows an implementation having no limiting character. In the figures.

DETAILED DESCRIPTION OF THE INVENTION

A particular field of application of the invention is that of determining the appearance of any losses of cohesion in a thermal barrier comprising a transparent ceramic layer formed on a substrate of monocrystalline metal superalloy with an interposed bonding underlayer.

Figure 1:
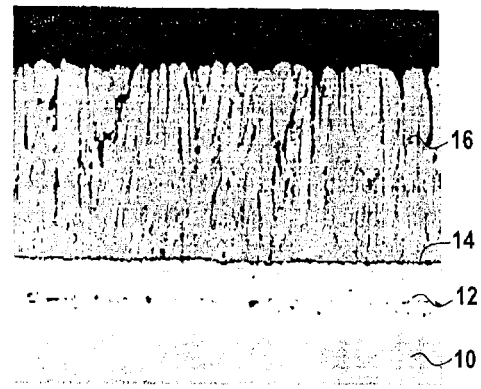
FIG. 1 is a section view of a substrate coated with a thermal barrier having a ceramic coating and on which the method of the invention can advantageously be performed.

FIG. 1 is a section view through an example of such a thermal barrier formed by a layer 16 of yttrium-stabilized zirconia. In this example, the layer 16 has a columnar structure obtained by an EBPVD deposition process. In another application, the zirconia layer could be obtained by means of a plasma (and therefore would not present a columnar structure).

The layer 16 is advantageously deposited on a bonding underlayer 12 made essentially of platinum-modified nickel aluminide (Ni,Pt)Al formed on a monocrystalline superalloy substrate 10. A layer or film 14 of alumina $Al_2O_3$ is formed at the interface between the bonding underlayer 12 and the zirconia layer 16 while the zirconia layer is being made. Such a structure is known, and for example it is described in document U.S. Pat. No. 5,843,585.

In a non-limiting implementation of the method of the invention, in order to cause losses of cohesion to appear in the thermal barrier layer, provision is made to apply a laser pulse to a substrate such as that shown in FIG. 1, for example. The application of a laser pulse and the effects it produces are known and described in particular in document FR 2 926 137, to which reference may be made.

Applying a laser pulse to the substrate is one way of causing losses of cohesion to appear in the ceramic coating layer in order to be able to determine its adhesion. Naturally, the present invention is not limited to such adhesion tests, but relates more generally to observing losses of cohesion, if any, in the ceramic coating layer, these losses of cohesion being capable of appearing in other ways. In particular, losses of cohesion may appear "naturally" during the lifetime of a thermal barrier, so that observing them serves to determine whether or not the barrier is properly held on the substrate.

In its application to performing such an adhesion test, a high energy short laser pulse is thus applied to the surface of the substrate 10 that is opposite from its surface having the coating 16. The laser energy is absorbed and generates plasma that, on expanding, creates compression waves. These compression waves give rise to a shock wave that propagates through the substrate and is then reflected by the free surface of the coating as an expansion wave. The expansion wave crossing through a wave corresponding to the end of the laser impulse gives rise to traction stresses that can lead to a loss of cohesion between the coating and the substrate, and more particularly in the example shown in FIG. 1, to localized rupturing of the bond between the zirconia layer 16 and the underlayer 12.

In accordance with the invention, means are provided for observing the surface of the zirconia coating layer, this observation serving to determine whether or not coating layer separation zones are present. In particular, in the absence of any separation of the zirconia layer, this layer, which is transparent, makes it possible to see the underlying layer, which is gray in color. In contrast, when a separation of the zirconia layer has been produced, a layer of air is present under the separated portion of the zirconia layer, which leads to a spot that is pale, with the area of that spot representing the magnitude of the separated portion.

Still in accordance with the invention, provision is made to view the image representative of a separation zone, if any, between the ceramic layer and the substrate at particular wavelengths that are longer than or equal to 500 nm.

The Applicant has found that observing the surface of the ceramic layer at wavelengths longer than or equal to 500 nm serves to improve the contrast between gray zones corresponding to no separation of the coating layer and pale zones corresponding to the presence of separation.

Figure 2A:
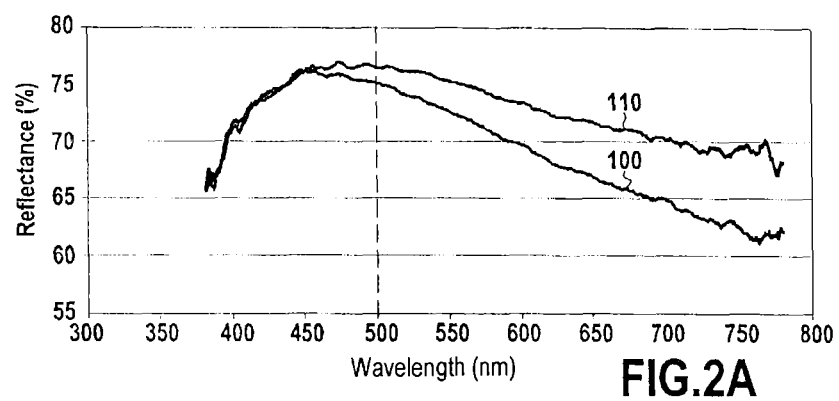
FIGS. 2A and 2B are curves showing reflectance as a function of wavelength for a thermal barrier with a columnar zirconia coating and with a plasma zirconia coating.
Figure 2B:
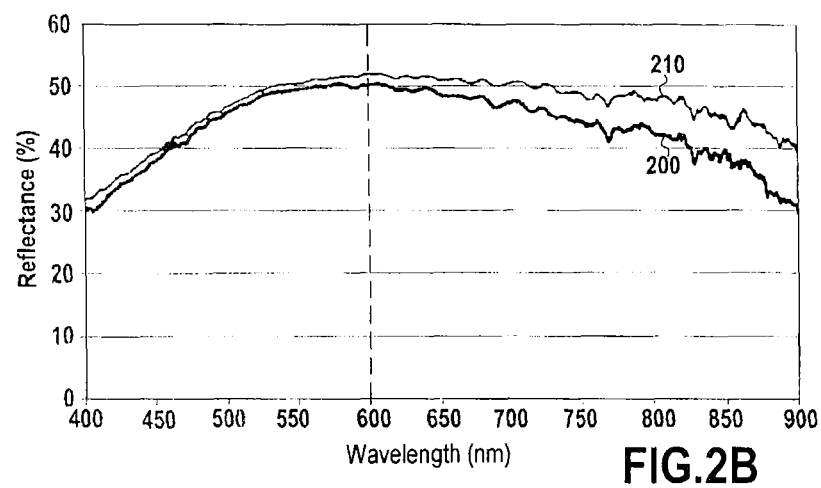

The curves plotted in FIGS. 2A and 2B reveal this remarkable feature of a coating layer of transparent ceramic. FIG. 2A shows in particular the reflectance (in percentage)—i.e. the proportion of incident light that is reflected by the coating layer—of a zirconia coating layer obtained by EBPVD deposition (giving it a columnar structure) as a function of wavelength (in nm), while FIG. 2B shows the reflectance for a zirconia coating layer obtained by plasma deposition.

In FIG. 2A, the curve 100 shows the reflectance of the EBPVD zirconia layer in the absence of separation, and the curve 110 shows the reflectance of the same layer in the presence of separation. These curves show clearly that the contrast between separation zones and zones without separation is very small or even non-existent for wavelengths shorter than 500 nm, and that it becomes more and more pronounced at wavelengths longer than these particular wavelengths.

In FIG. 2B, the curve 200 shows the reflectance of the plasma zirconia layer in the absence of separation, and the curve 210 shows the reflectance of the same layer in the presence of separation. These curves show that ever increasing contrast appears at wavelengths longer than or equal to 600 nm.

Thus, by using wavelengths longer than or equal to 500 nm, it is possible to increase greatly the contrast between zones in which the coating layer has separated and zones without separation. This makes it much easier to see the spots corresponding to separation zones. The same applies to estimating the dimensions of such spots, which dimensions are characteristic of the magnitude of the separated portion.

The surface of the ceramic layer may be observed at the above-mentioned particular wavelengths in various ways.

In one implementation, provision is made to subject the coating layer to narrow spectrum lighting at wavelengths longer than or equal to 500 nm, the image of the surface of the coating layer being captured by a conventional digital camera.

In another implementation, the coating layer is subjected to white lighting (i.e. covering the entire visible electromagnetic spectrum), the image of the surface of the coating layer being picked up by a digital camera. Furthermore, a filter that passes only the particular wavelength (i.e. longer or equal to 500 nm) is interposed between the camera and the substrate in order to retain only images at the desired wavelengths.

In yet another implementation, the coating layer is subjected to white lighting, the image being picked up by a camera having optical sensors that are adjusted to the particular wavelengths (i.e. longer than or equal to 600 nm).

Images of the surface of the ceramic layer at the particular wavelengths may be used in a manner similar to that described in document FR 2 926 137. In particular, by performing a destructive test on a sample or a part, it is possible to determine an adhesion threshold for a coating by measuring the area of a spot representing separation caused by an impact from laser radiation. It is thus possible, after experimentally correlating between the applied laser energy with an adhesion threshold for a coating formed by a given method, to perform non-destructive tests by subjecting parts to laser energy at a level that is determined as a function of the level corresponding to the adhesion threshold. The correlation between the laser energy level and the adhesion threshold can be obtained experimentally by analyzing the size of an observed spot or by sweeping through a set of different energy levels and determining the limit at which a pale spot appears.

The invention claimed is:

1. A method of determining appearance of loss of cohesion in a transparent ceramic coating layer on a substrate, the method comprising:
   detecting an image representative of a separation zone between the transparent ceramic coating layer and the substrate; and
   analyzing the image by viewing the image optically at particular wavelengths of longer than or equal to 500 nm, in order to determine the loss of cohesion in the transparent ceramic coating layer on the substrate,
   wherein:
   the transparent ceramic coating layer is subjected to white lighting; and
   the image is captured by a camera.

2. The method according to claim 1, wherein
   the transparent ceramic coating layer comprises zirconia obtained by a plasma deposition process, and
   the particular wavelengths are longer than or equal to 600 nm.

3. The method according to claim 1, wherein the transparent ceramic coating layer comprises zirconia obtained by an EBPVD deposition process.

4. The method according to claim 1, wherein
   the transparent ceramic coating layer is subjected to the white lighting, and
   the image is captured by a camera with a filter at the particular wavelengths being interposed between the camera and the substrate.

5. The method according to claim 1, wherein
   the transparent ceramic coating layer is subjected to the white lighting, and
   the image is captured by a camera having optical sensors adjusted to the particular wavelengths.

* * * * *